United States Patent
Addington et al.

(10) Patent No.: US 8,652,066 B2
(45) Date of Patent: *Feb. 18, 2014

(54) INVOLUNTARY CONTRACTION INDUCED PRESSURE AS A MEDICAL DIAGNOSTIC TOOL

(75) Inventors: W. Robert Addington, Melbourne Beach, FL (US); Robert E. Stephens, Parkville, MO (US)

(73) Assignee: Pneumoflex Systems, LLC, Melbourne, FL (US)

( * ) Notice: Subject to any disclaimer, the term of this patent is extended or adjusted under 35 U.S.C. 154(b) by 670 days.

This patent is subject to a terminal disclaimer.

(21) Appl. No.: 11/608,316

(22) Filed: Dec. 8, 2006

(65) Prior Publication Data

US 2007/0135736 A1    Jun. 14, 2007

Related U.S. Application Data

(60) Provisional application No. 60/748,892, filed on Dec. 9, 2005.

(51) Int. Cl.
*A61B 5/20* (2006.01)
*A61B 5/03* (2006.01)

(52) U.S. Cl.
USPC ............................................. 600/561

(58) Field of Classification Search
USPC ............................................. 600/561
See application file for complete search history.

(56) References Cited

U.S. PATENT DOCUMENTS

| | | | |
|---|---|---|---|
| 2,918,893 A | 12/1959 | Norton | |
| 3,286,713 A | 11/1966 | Kurtz et al. | |
| 3,373,735 A | 3/1968 | Gallagher | |
| 3,426,758 A | 2/1969 | Harautuneian | |
| 3,895,629 A | 7/1975 | Snyder | 128/171 |
| 4,080,970 A | 3/1978 | Miller | 128/350 |
| 4,214,593 A | 7/1980 | Imbruce et al. | 128/748 |
| 4,221,215 A | 9/1980 | Mandelbaum | 128/155 |
| 4,613,323 A | 9/1986 | Norton et al. | 604/43 |
| 4,632,119 A | 12/1986 | Reichstein | 128/632 |

(Continued)

FOREIGN PATENT DOCUMENTS

| | | | | |
|---|---|---|---|---|
| EP | 0 608 593 | 8/1994 | ............... | A61B 5/20 |
| EP | 0 694 284 | 1/1996 | ........... | A61B 5/0215 |

(Continued)

OTHER PUBLICATIONS

WD. Man et al., "Cough Gastric Pressure and Maximum Expiratory Mouth Pressure in Humans", American Journal of Respiratory and Critical Care Medicine, vol. 168, 2003, 4 pages.

(Continued)

*Primary Examiner* — Rene Towa
*Assistant Examiner* — Emily Lloyd
(74) *Attorney, Agent, or Firm* — Allen, Dyer, Doppelt, Milbrath & Gilchrist, P.A.

(57) ABSTRACT

Techniques for detecting stress urinary incontinence use a pressure sensing catheter the electrical indications of which are applied to a processing unit for detecting pressure levels generated during involuntary coughs. The involuntary coughs are induced preferentially by using a nebulized composition of L-tartrate in a pharmaceutically acceptable carrier. The area under the curve generated from pressure samples is calculated and used in conjunction with the detection of urine leakage to determine the existence of stress urinary incontinence.

2 Claims, 3 Drawing Sheets

(56) References Cited

U.S. PATENT DOCUMENTS

| | | | |
|---|---|---|---|
| 4,790,328 A * | 12/1988 | Young | 600/561 |
| 4,973,314 A | 11/1990 | Garret | 604/180 |
| 4,976,261 A | 12/1990 | Gluck et al. | 128/207.15 |
| 5,146,916 A | 9/1992 | Catalani | 128/207.14 |
| 5,433,216 A | 7/1995 | Sugrue et al. | 128/778 |
| 5,462,539 A | 10/1995 | Herman et al. | 604/385.1 |
| 5,862,804 A | 1/1999 | Ketchum | 128/885 |
| 5,904,656 A | 5/1999 | Addington et al. | 600/529 |
| 5,904,666 A | 5/1999 | Dedecker et al. | 604/65 |
| 5,947,943 A | 9/1999 | Lee | 604/361 |
| 5,980,507 A | 11/1999 | Fassuliotis et al. | 604/540 |
| 6,004,268 A | 12/1999 | Addington et al. | 600/300 |
| 6,056,699 A | 5/2000 | Sohn et al. | 600/561 |
| 6,267,729 B1 * | 7/2001 | Addington et al. | 128/898 |
| 6,284,942 B1 | 9/2001 | Rabin | 604/361 |
| 6,561,195 B2 | 5/2003 | Addington et al. | 128/898 |
| 6,568,397 B1 | 5/2003 | Addington et al. | 128/897 |
| 6,581,605 B2 | 6/2003 | Addington et al. | 128/897 |
| 6,655,376 B2 | 12/2003 | Addington et al. | 128/200.24 |
| 6,679,249 B2 | 1/2004 | Addington et al. | 128/200.14 |
| 6,863,664 B2 | 3/2005 | Wada et al. | 604/385.17 |
| 7,140,370 B2 | 11/2006 | Tresnak et al. | 128/207.14 |
| 7,311,696 B2 | 12/2007 | Christon et al. | 604/385.01 |
| 7,322,359 B2 | 1/2008 | Ketchum | 128/886 |
| 7,332,642 B2 | 2/2008 | Liu | 604/361 |
| 7,343,915 B2 | 3/2008 | Addington et al. | 128/203.12 |
| 7,794,425 B2 | 9/2010 | Gobel | 604/101.05 |
| 2001/0050086 A1 | 12/2001 | Addington et al. | 128/898 |
| 2002/0049425 A1 * | 4/2002 | Mosel et al. | 604/517 |
| 2002/0112731 A1 | 8/2002 | Ketchum | 128/866 |
| 2003/0028075 A1 | 2/2003 | Ulmsten et al. | 600/29 |
| 2003/0078553 A1 | 4/2003 | Wada et al. | 604/361 |
| 2003/0114809 A1 | 6/2003 | Gagliardi et al. | 604/361 |
| 2004/0015100 A1 | 1/2004 | Schmidt | 600/561 |
| 2004/0116457 A1 * | 6/2004 | Ishihara et al. | 514/290 |
| 2004/0133067 A1 * | 7/2004 | Tracey | 600/29 |
| 2004/0172010 A1 * | 9/2004 | Addington et al. | 604/890.1 |
| 2004/0267336 A1 | 12/2004 | Morrison et al. | 607/99 |
| 2005/0038328 A1 | 2/2005 | Stoehrer et al. | 600/301 |
| 2005/0059900 A1 | 3/2005 | Berger et al. | 600/546 |
| 2005/0065450 A1 | 3/2005 | Stuebe et al. | 600/547 |
| 2007/0123793 A1 | 5/2007 | Addington et al. | 600/546 |
| 2007/0225576 A1 | 9/2007 | Brown et al. | 600/301 |
| 2008/0077043 A1 | 3/2008 | Malbrain et al. | 600/547 |
| 2008/0208151 A1 | 8/2008 | Zacharias et al. | 604/361 |
| 2008/0255529 A1 | 10/2008 | Christon et al. | 604/361 |
| 2008/0255530 A1 | 10/2008 | Christon et al. | 604/361 |
| 2008/0262454 A1 | 10/2008 | Christon et al. | 604/361 |

FOREIGN PATENT DOCUMENTS

| | | | |
|---|---|---|---|
| WO | 99/53837 | 10/1999 | A61B 5/08 |
| WO | 03/092495 | 11/2003 | A61B 5/05 |
| WO | 2004/073516 | 9/2004 | A61B 5/08 |
| WO | 2007/081626 | 7/2007 | A61B 5/100 |
| WO | 2008/094771 | 8/2008 | A61B 10/00 |

OTHER PUBLICATIONS

Martin et al., "*Systematic Review and Evaluation of Methods of Assessing Urinary Incontinence*," Health Technology Assessment 2006, vol. 10, No. 6, Feb. 2006, 121 pages.

Vovk et al., "*Capsaicin Exposure Elicits Complex Airway Defensive Motor Patterns in Normal Humans in a Concentration-Dependent Manner*," Pulm Pharmacol Ther. 2007; 20(4):423-32, Epub, Dec. 12, 2006, Abstract Only, 2 pages.

Lavorini at al., "*Fog-Induced Cough with Impaired Respiratory Sensation in Congenital Central Hypoventilation Syndrome*," Am J Respir Crit Care Med., Oct. 15, 2007; 176(8):825-32. Epub, Aug. 2007, Abstract Only, 2 pages.

Lasserson et al., "*Differences in Motor Activation of Voluntary and Reflex Cough in Humans*," Thorax, Aug. 2006; 61(8):699-705. Epub, Apr. 6, 2006, Abstract Only, 2 pages.

Steier et al. "The Value of Multiple Tests of Respiratory Muscle Strength," Thorax, Jun. 8, 2007 Epub, Abstract Only, 2 pages.

"*Urinary Incontinence in Women*" American Family Physician: American Family Physician vol. 62, No. 11 Dec. 1, 2000.

"*Exercising Your Pelvic Muscles*" American Family Physician: American Family Physician vol. 62, No. 11 Dec. 1, 2000.

Azpiroz et al. "*Anorectal Functional Testing: Review of Collective Experience*" PMID: 11866256; Am. J. Gastroenterol. Feb. 2002; 97(2)L 2320-240. (Abstract Only).

Bolster et al. "*Responses of the Anterolateral Abdominal Muscles During Cough and Expiratory Threshold Loading in the Cat*" Journal of Applied Physiology 88: 1207-1214, 2000.

Brown et al. "*Prevalence of Urinary Incontinence and Associated Risk Factors in Postmenopausal Women*" Obstetrics & Gynecology: 1999: 94: 66-70.

Bump et al. "*Valsalva Leak Point Pressures in Women With Genuine Stress Incontinence: Reproducibility, Effect of Catheter Caliber, and Correlations With Other Measures of Urethral Resistance. Continence Program for Women Research Group*" Am. J. Obstet. Gynecol. Aug. 1995; 173(2):551-7. (Abstract Only).

Carry et al. "*Intra-abdominal Pressure*" Ann. Fr. Aneshth. Ranim. 1994; 13(3): 381-99. (Abstract Only).

Chang et al. "Transrectal Sonographic Cystourethrography: Studies in Stress Urinary Incontinence" ScienceDirect-Urology; vol. 36, Issue 6, Dec. 1990, pp. 488-492. (Abstract Only).

Chiara et al. "*Expiratory Muscle Strength Training in Persons With Mulitple Sclerosis Having Mild to Moderate Disability: Effect on Maximal Expiatory Pressure, Pulmonary Function, and Maximal Voluntary Cough*" Arch Phys Med REhabil. vol. 87, Apr. 2006 pp. 468-473.

Ciofu et al. "*Contribution of VLPP (Valsalva Leak Point Pressure) in the Urodynamic Assessment*" Gynecol. Obstet. Fertil. Feb. 2004; 32(2): 160-3. (Abstract Only).

Culligan et al. "*Urinary Incontinence in Women: Evaluation and Management*" American Family Physician, vol. 62 No. 11. Dec. 1, 2000.

Freestone et al. "*Assessment of the Antitussive Efficacy of Codeine in Cough Associated with Common Cold*" PubMed: J. Pharm. Pharmacol. Oct. 1997; 49(10) 1045-1049. (Abstract Only).

Hammond et al. "*Assessment of aspiration risk in stroke patients with quantification of voluntary cough*" American Academy of Neurology. www.neurology.org 2001;56;502-506.

Hundley et al. "*A Multicentered Comparison of Measurements Obtained with Microtip and External Water Pressure Transducers*" PubMed: Int. Urogynecol. J. Pelvic Floor Dystfunct. Nov. 12, 2005; 1-7. (Abstract Only).

Kim et al. "*The Vesico-Urethral Pressuregram Analysis of Urethral Function Under Stress*" ScienceDirect; Journal of Biomechanics, vol. 30. Issue 1, Jan. 1997, pp. 19-25. (Abstract Only).

Kocjancic et al. "*Evaluation of Minimally Invasive Analysis System for Cough Leak Point Pressure Measurement*" PubMed: J. Uro. Sep. 2004; 172(3): 994-7. (Abstract Only).

Langdon et al. "*High Incidence of Respiratory Infections in 'Nil by Mouth' Tube-Fed Acute Ischemic Stroke Patients*" Neuroepidemiiology 2009; 32: 107-113.

Majoros et al. "*Value of Testing the Abdominal Leak Point Pressure in the Differential Diagnosis of Urinary Stress Incontinence*" PubMed: Orv. Hetil. Nov. 23, 2003; 144(47): 2321-5. (Abstract Only).

Martin, et al. "Systematic review and evaluation of methods of assessing urinary incontinence" Health Technology Assessment, Feb. 2006. vol. 10, No. 6.

Matthys et al. "*Objectivation of the Effect of Antitussive Agents Using Tussometry in Patients with Chronic Cough*" PubMed: Schweiz Med Wochenschr. Mar. 2, 1985; 115(9): 307-11. (Abstract Only).

McEwan, Jr. et al. "*Change in Cough Reflex after Treatment with Enalapril and Ramipril*" PubMed: BMJ. Jul. 1, 1989; 299(6690): 13-6. (Abstract Only).

Miklos, Jr. et al. "*A Critical Appraisal of the Methods of Measureing Leak-Point Pressures in Women with Stress Incontinence*" PubMed: Obstet. Gynecol. Sep. 1995; 86(3): 349-52. (Abstract Only).

Phua, et al. "*Patients with Gastro-Oesophageal Reflux Disease and Cough have Impaired Laryngopharyngeal Mechanosensitivity*" PubMed: Thorax. Jun. 2005; 60(6): 488-91. (Abstract Only).

(56) References Cited

OTHER PUBLICATIONS

Quek, et al. "*Morbidity and Significant Bacteriuria after Urodynamic Studies*" Annals Academy of Medicine; Singapore 2004; 33:754-7.

Shaker, et al. "*Vocal Cord Closure Pressure During Volitional Swallow and other Voluntary Tasks*" PubMed: Dysphagia. Winter 2002; 17(1)L 13-8. (Abstract Only).

Steffen, et al. "*Measurement of Pressure and Force as a Basis of the Postoperative Evaluation of Abdominal Wall Function*" PubMed: Z. Exp. Chir. Transplant. Kunstliche Organe. 1987; 20(1): 44-9. (Abstract Only).

Swift et al. "*Test-retest Reliability of the Cough Stress Test in the Evaluation of Urinary Incontinence*" Obstetrics and Gynecology; vol. 94, No. 1, Jul. 1999; pp. 99-102.

Van Hengstum, et al. "*Effect of Positive Expiratory Pressure Mask Physiotherapy (PEP) Versus Forced Expiration Technique 9FET/PD) on Regional Lung Clearance in Chronic Bronchitics*" PubMed: Eur. Erspir. J. 1991; 4(6): 651-4. (Abstract Only).

Wall, et al. "*Are Vaginal and Rectal Pressures Equivalent Approximations of One Another for the Purpose of Performing Subtracted Cystometry?*" PubMed: Obstet. Gynecol. Apr. 1995; 85(4):488-93. (Abstract Only).

Addington at al. "*Intra-abdominal Pressures during Voluntary and Reflex Cough*" Cough: vol. 4, 2, Apr. 30, 2008; pp. 1-9.

Cormier et al., "*Diagnosis of Female Bladder Outlet Obstruction and Relevance of the Parameter Area Under the Curve of Detrusor Pressure During Voiding: Preliminary Results*," Journal of Urology, May 2002, vol. 167, pp. 2083-2087.

Lasserson et al., "*Differences in Motor Activation of Voluntary and Reflex Cough in Humans*," Thorax, Aug. 2006; 61(8):699-705. Epub, Apr. 6, 2006.

WD. Man et al., "Cough Gastric Pressure and Maximum Expiratory Mouth Pressure in Humans", American Journal of Respiratory and Critical Care Medicine, vol. 168, 2003.

Cadiere et al. "*Antireflux Transoral Incisionless Fundoplication Using EsophyX: 12-Month Results of a Prospective Multicenter Study*" World J Surg (2008) 32:1676-1688.

Marino et al. "*Induction of Lower Esophageal Sphincter (LES) Dysfunction during Use of the Negative Pressure Body Ventilator*" The American Journal of Gastroenterology vol. 83, No. 12, 1988.

"*GERD*" http://www.endogartricsolutions.com/aboutGERD_for-surgeons.htm.

Jones et al. "*Mechanisms of Pelvic Floor Muscle Function and the Effect on the Urethra during a Cough*" www.sciencedirect.com.

Chang et al. "*An objective study of acid reflux and cough in children using an ambulatory pHmetry-cough logger*" http://adc.bmj.com/cgi/reprintform.

Vizel et al. "*Validation of an ambulatory cough detection and counting application using voluntary cough under different conditions*" Http://www.coughjournal.com/content/6/1/3.

Ryan et al. "*Cough reflex sensitivity improves with speech language pathology management of refractory chronic cough*" http://www.coughjournal.com/content/6/1/5.

Canning et al. "*An essential component to brainstem cough gating identified in anesthetized guinea pigs*" The FASEB Journal article fj.09-151068.

F. Lavorini et al., "Fog-Induced Cough with Impaired Respiratory Sensation in Cogenital Central Hypoventilation Syndrome", Am J Respir Crit Care Med., Oct. 15, 2007; 176(8):825-32. Epub Aug. 2007.

Cobb et al., "*Normal Intraabdominal Pressure in Healthy Adults*," Journal of Surgical Research, vol. 129, Feb. 18, 2005, pp. 231-235.

Upadya et al., "*Predictors and Consequences of Pneumonia in Critically Ill Patients With Stroke*," Journal of Critical Care, vol. 19, No. 1, Mar. 2004, pp. 16-22.

Bolster et al. "*Neurogenesis of cough, other airway defensive behaviors and breathing: A holarchical system?*" Jan. 16, 2006 www.sciencedirect.com.

DeBacker "*Abdominal compartment syndrome*" http://ccforum.com. Sep. 30, 1999.

Dziewas et al. *Pneumonia in acute stroke patients fed by nasogastric tube* www.jnnp.com Sep. 10, 2003.

Irwin, Richard "*Chronic Cough Due to Gastroesophageal Reflux Disease: ACCP Evidence-Based Clinical Practice Guidelines*" http://chestjournal.chestpubs.org/content/129/1_supII/80S.full.html.

Irwin et al. "*The Cough Reflex and Its Relation to Gastroesophageal Reflux*" Am J Med. 2000;108(4A):73S-78S.

Handa et al. "*Federal Guidelines for the Management of Urinary Incontinence in the United States: Which Patients Should Undergo Urodynamic Testing?*" Int. Urogynecol J (1995) 6:198-203.

Jakus et al. "*Brainstem Areas Involved in the Aspiration Reflex: c-Fos Study in Anesthetized Cats*" Physiol. Res. 53: 703-717, 2004.

Poliacek et al. "*Cough, Expiration and Aspiration Reflexes following Kainic Acid Lesions to the Pontine Respiratory Group in Anesthetized Cats*" Physiol. Res. 53: 155-163, 2004.

Widdicombe et al. "*Supramedullary influences on cough*" Respiratory Physiology Neurobiology 152 (2006) 320-328.

\* cited by examiner

```
┌─────────────────────────────┐
│   Administer a nebulized    │
│   composition of L-tartrate in a │ ─── 200
│   pharmaceutically acceptable carrier │
└─────────────────────────────┘
              │
              │
┌─────────────────────────────┐
│  Record bladder pressure curves │
│  during involuntary cough induced │ ─── 210
│           by step 1         │
└─────────────────────────────┘
              │
              │
┌─────────────────────────────┐
│    Note any urinary leakage │ ─── 220
└─────────────────────────────┘
```

FIGURE 2

INVOLUNTARY CONTRACTION INDUCED PRESSURE AS A MEDICAL DIAGNOSTIC TOOL

CROSS REFERENCE TO RELATED APPLICATIONS

This application claims priority to and incorporates by reference in its entirety U.S. Provisional Application Ser. No. 60/748,892, filed Dec. 9, 2005, entitled Involuntary Contraction-Induced Pressure as a Medical Tool by inventors W. Robert Addington and Robert Stephens, which is incorporated herein by reference in its entirety.

BACKGROUND OF THE INVENTION

1. Field of the Invention

This invention relates to medical diagnostic tests and, more specifically, to a diagnostic test for evaluating a neurological deficiency in a patient by inducing an involuntary abdominal contraction and obtaining a measurement of pressure generated by the involuntary contraction.

2. Description of the Prior Art

People may experience many different types of neurological deficiencies. One common type, for example, is the iatrogenic neurological deficiency caused by general anesthesia. Another example includes urinary incontinence, where a patient loses either complete or partial bladder control due to nerve damage of some sort. Still another example may be the stroke victim who has lost muscle strength and tone along one side of the body, consequently being unable to contract at least half the muscles which help produce a cough forceful enough to properly clear the respiratory airways.

For example, a patient experiencing urinary incontinence must be properly diagnosed to identify the specific type of incontinence from which the patient suffers. The treatments may be different, depending on the type of incontinence. Therefore, proper diagnosis becomes important at least for that reason.

Stress incontinence is a condition believed to result primarily in older women due to loss of extrinsic support for the pelvic organs and for the neck of the bladder. The tissues of the pelvis and of the distal urethra contain estrogen and progesterone receptors. Following menopause and decrease of the hormones, the tissues of the urethra may lose resiliency and become somewhat flaccid. Under those conditions, any increase in intra-abdominal pressure causes urine in the bladder to be pushed outwardly as resistance in the urethra is overcome, resulting in leakage of urine. This condition is known as stress incontinence and occurs in the absence of contractions by the detrusor muscle of the bladder. Stress incontinence may be responsive to treatment with exogenous estrogens, although this is not an effective treatment for all patients, particularly depending on age. Alternative treatments may include pelvic muscle exercises, a-adrenergic agents, such as phenylpropanolamine, that act on the a-adrenergic receptors along the urethra and increase urethral tone.

The most common cause of urinary incontinence, however, is detrusor hyperreflexia, or hyperactivity of the detrusor muscle. This type of incontinence is believed to result from lack of inhibition of the detrusor muscle due to a decreased detrusor reflex in the brain stem. Nevertheless, in most affected elderly there appears to be no underlying neurological defect. In this condition, treatment may include antispasmodic agents which tend to relax the wall of the bladder.

A typical test employed to distinguish these two types of urinary incontinence is one which increases intra-abdominal pressure so as to, in turn, put pressure on the bladder. The Valsalva maneuver is one such test. This procedure is named after Antonio M. Valsalva, an Italian anatomist of the late seventeenth and early eighteenth centuries. In this technique, the patient generates a muscular contraction of the chest, abdomen and diaphragm in a forced expiration against a closed glottis. This increases pressure within the thoracic cavity and also in the abdominal cavity. The Valsalva maneuver also refers to raising the pressure in the nasopharynx by a forced expiration with the mouth closed and the nostrils pinched, for example, to clear the patency of the Eustachian tubes. Other testing techniques involve having the patient jump up and down to jostle the bladder, or bend down so as to compress the abdomen. Yet another method involves having the patient generate one or more strong voluntary coughs.

It is known, however, that some patients are unable to perform these physical acts. For example, a patient may not be able to jump, or to bend, or to generate a strong voluntary cough. Additionally, there are some patients who will not be correctly diagnosed on the basis of the cough test, perhaps because their coughs are insufficiently strong. Accordingly, there is a need for alternative or supplementary tests that will aid in diagnosing urinary stress incontinence.

As noted above, however, other clinical diagnostic tests also rely on the patient's ability to generate a forceful volitional abdominal contraction or Valsalva maneuver as an identifier of normal neurological and/or muscular function. Many patients, however, are unable to produce a forceful voluntary abdominal contraction or voluntary Valsalva maneuver and the associated diagnosis may be hampered or missed altogether.

A rather complete discussion of methods of evaluating urinary incontinence is found in a February 2006 article by JL Martin et al. entitled "Systematic review and evaluation of methods of assessing urinary incontinence (hereinafter referred to as Systematic review)."

Problems of the Prior Art

One of the problems associated with the prior art techniques is that some patients are unable or are unwilling to perform the physical acts to the extent needed. For example, a patient may not be able to jump, or to bend, or to generate a strong voluntary cough. Some patients may be able to perform these acts, but be unwilling to do so because, in the use of stress incontinence, an involuntary release of urine may be embarrassing or contrary to what is considered proper in society.

BRIEF SUMMARY OF THE INVENTION

Various aspects of the invention are directed toward an apparatus and techniques for evaluating neurological deficiency, such as iatrogenic neurological deficiency caused by general anesthesia, urinary incontinence (full or partial) caused by nerve damage, or loss of muscular control caused by stroke.

BRIEF DESCRIPTION OF THE DRAWINGS

The invention will be described more in detail with reference to the following drawings.

FIG. 2 shows a flow chart of a technique for conducting a reflexive cough test (RCT).

DETAILED DESCRIPTION OF THE INVENTION

Figure 1:
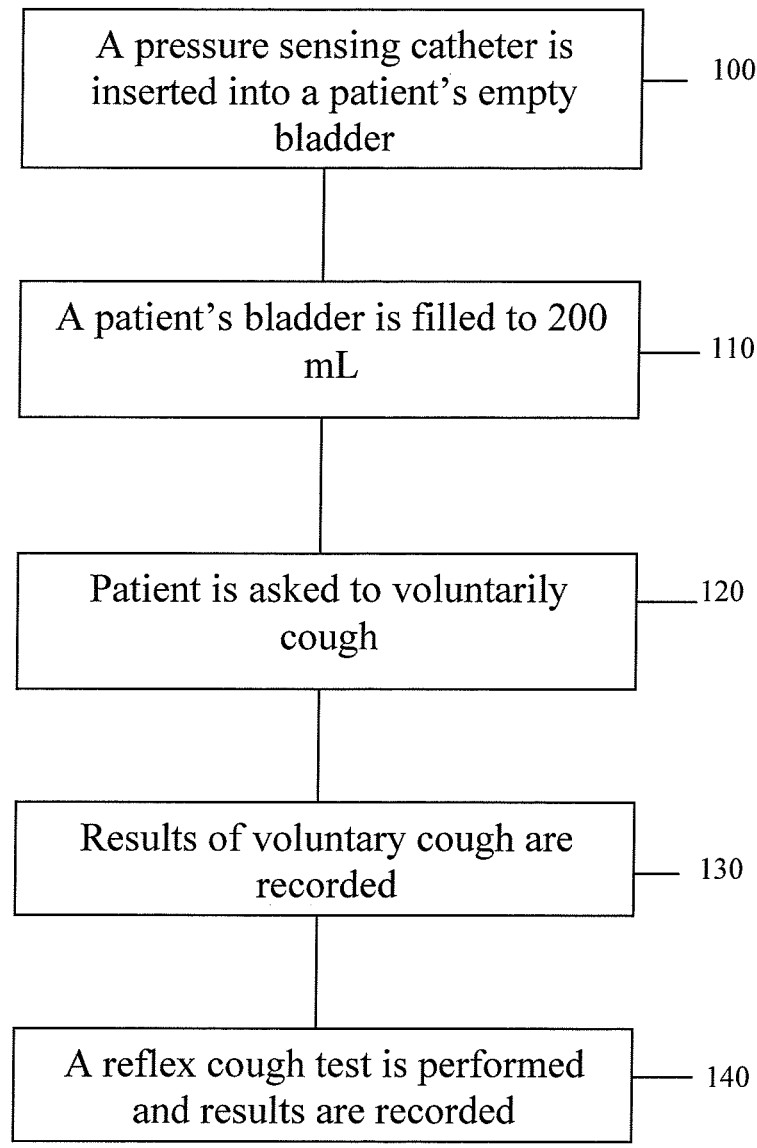
FIG. 1 shows a flow chart of a technique for evaluating a patient for urinary stress incontinence in accordance with one aspect of the invention.

The present invention seeks to provide a clinical test which depends neither on the patient's ability to generate a forceful volitional abdominal contraction or Valsalva maneuver nor on personal observation by the physician to make the diagnosis. The method of the invention includes positioning a pressure transducer in a patient being evaluated and inducing an involuntary abdominal contraction. In one embodiment of the present invention, the involuntary contraction may be initiated through induction of an involuntary cough by any suitable means. For example, a chemoirritant may be introduced into the patient's upper airway. Mechanical stimulation may be employed, for example, by use of an endoscope. Other stimuli may also be employed, for example, electrical stimulation of the abdominal muscles to produce an involuntary Valsalva maneuver, etc.

The skilled will recognize that the induction of an involuntary cough is but one method of generating an involuntary abdominal contraction and that the invention is not limited to any one specific method of doing so. It is important, however, that the contraction be an involuntary response that does not require the patient's volitional cooperation. Additionally, it is also important that the pressure generated by the involuntary abdominal contraction be measured. The skilled will further understand that such a pressure measurement may be obtained by any one of a variety of devices and processes, most typically by a pressure transducer, although the invention is not intended to be limited to such.

As noted, one approach to generating the involuntary abdominal contraction, or Valsalva maneuver, would be by having the patient breathe an aerosol containing a chemoirritant agent effective for causing the involuntary cough and obtaining a measure of the pressure generated by the involuntary cough. Placement of the transducer in the body of the patient will depend on the specific neurological deficit being evaluated. The transducer may be placed intrarectally, for example. The agent effective for inducing an involuntary cough may be any one of several known to the skilled, for example, tartaric acid, capsaicin, citric acid, saline, distilled water, powders of various types, and others.

Whatever the method of induction, whether involuntary chemoirritant induced cough, eletrical stimulus or mechanical stimulation, because the contraction produced is involuntary, any uncertainty as to the degree of patient cooperation is eliminated. Further, since patient cooperation in producing a involuntary contraction is not needed, the test may be applied to patients who may be under sedation, for example, a patient who may have had a spinal anesthetic. Similarly, a patient who has had a stroke and who has lost volitional muscle control on one side of the body will still be able to produce an involuntary abdominal contraction, for example, an involuntary cough, albeit having a lower expiratory pressure.

The pressure produced by the involuntary abdominal contraction will be sensed by a pressure transducer placed in the patient's body and provides a quantitative, non-subjective measure by which the patient's condition may be determined. A population of healthy, non-smoking, normal individuals would be expected to produce a range of involuntary contraction-induced pressures displaying the typical bell-shaped curve. It is also predicted that there will probably be one normal curve or range for males and a slightly different normal curve or range for females.

Comparing the involuntary contraction-induced pressure generated by a patient to the normal distribution, it would be possible to classify the patient to be either within the normal range or outside the normal range and this could be done with a large degree of certainty based on objectively measured pressures, rather than more subjectively based on skilled observation.

The presently described diagnostic test could be used to quantify loss of function or, conversely, return of function following a loss. For example, in a stroke patient, measurement of the involuntary contraction-induced pressure could be used to monitor the return of muscle tonicity and control during recovery. Expiratory pressure readings would be indicative of whether the patient has sufficient ability to clear the airway and, consequently, whether the patient is recovering or whether the patient requires continued ventilatory assistance.

In another example, the presently described test could be applied to a patient undergoing surgery for strengthening the support of the neck of the bladder so as to correct urinary incontinence. The patient would most likely have received a spinal anesthetic but may not be easily able to produce a voluntary cough while on the operating table so as to test the effectiveness of the repair. The patient could be administered a cough-inducing inhalant while the intrarectal pressure is monitored. The pressure reading would indicate whether a normal pressure was reached during the cough and the surgeon could monitor whether there was bladder leakage during the cough. Leakage occurring during an induced cough generating normal pressure would definitely indicate that the repair has not been effective. The surgeon would then have the opportunity of realigning the repair in order to make it effective, this with the patient still on the surgical table.

FIG. 1 shows a flow chart of a technique for evaluating a patient for urinary stress incontinence in accordance with one aspect of the invention. As an initial step, a pressure sensing catheter is inserted into a patient's empty bladder (100). The patient's bladder is then filled slowly with sterile water until 200 ml have been delivered (110).

The patient is then asked to voluntarily cough (120) and the results of the voluntary cough are recorded (130) by recording the variations in pressure as a function of time and by recording whether or not the cough induced involuntary expulsion of urine.

Then, a reflex cough test is performed (140) and the results are recorded in a manner substantially similar to step 130. Details of the reflex cough tests are discussed more in conjunction with FIG. 2.

FIG. 2 shows a flow chart of a technique for conducting a reflex cough test. With the test arrangement in place as described in conjunction with items 100 and 110 of FIG. 1, instead of asking a patient to voluntarily cough, the patient is administered a nebulized composition of L-tartrate in a pharmaceutically acceptable carrier (200). The variations in bladder pressure that occur during the involuntary coughs induced by step 200 are then recorded and plotted for display (210). The patient is checked for any urinary leakage that occurs during the involuntary coughs (220).

Figure 3:
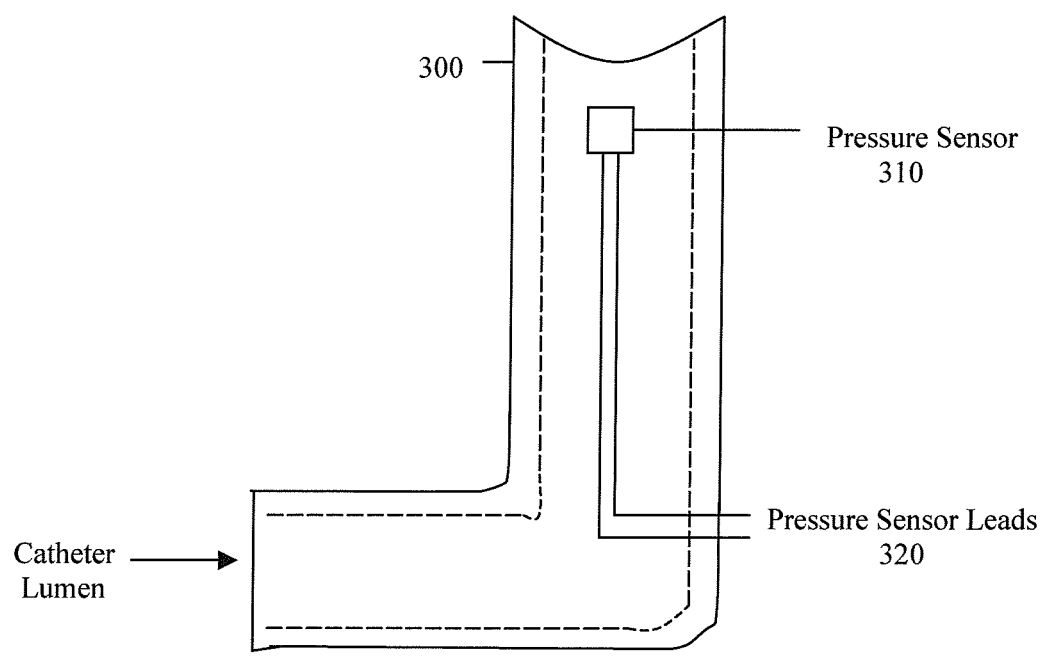
FIG. 3 shows a catheter that can be used for carrying out various aspects of the invention.

FIG. 3 shows a catheter that can be used for carrying out various aspects of the invention. A catheter, 300, includes a pressure sensor 310 and conductive wires or paths which conduct the electrical output of the pressure sensor 310 to external circuitry. The wires or paths are hereinafter called pressure sensor leads 320. The catheter lumen can be utilized to fill or drain the patient's bladder as appropriate. Examples of a catheter usable in accordance with the invention may include a Foley catheter equipped with a pressure sensor.

The present invention has been described above, in which description preferred embodiments of the invention are discussed. Unless otherwise defined, technical and scientific terms used herein have the same meaning as commonly understood by one of ordinary skill in the art to which this invention pertains. Although methods and materials similar or equivalent to those described herein can be used in the practice or testing of the present invention, suitable methods and materials are described above. In addition, the materials, methods and examples given are illustrative in nature only and not intended to be limiting. Accordingly, this invention may be embodied in many different forms and should not be construed as limited to the illustrated embodiments set forth herein. Rather, these illustrated embodiments are provided solely for exemplary purposes so that this disclosure will be thorough and complete, and will fully convey the scope of the invention to those skilled in the art. Other features and advantages of the invention will be apparent from the above detailed description, and from the claims.

What is claimed is:

1. A method for evaluating for stress urinary incontinence in a patient, comprising:

inserting a pressure sensing catheter within a patient's bladder, the pressure sensing catheter having a pressure sensor on the surface of the catheter and positioned within the patient's bladder for measuring bladder pressure;

filling the patient's bladder to a predetermined level;

having the patient voluntarily cough to produce a voluntary cough event;

measuring the variations of bladder pressure as a function of time for the duration of the voluntary cough event using the pressure sensing catheter and determining whether or not the voluntary cough event induced involuntary expulsion of urine;

supplying to the throat of the patient an aerosol containing a chemoirritant agent effective for inducing at least one involuntary cough event;

measuring the variations of bladder pressure as a function of time during the at least one involuntary cough event using the pressure sensing catheter and determining whether or not the at least one involuntary cough event induced an involuntary expulsion of urine; and processing the measured variations of bladder pressure over time for both the voluntary cough event and the at least one involuntary cough event and whether or not the voluntary cough event and involuntary cough event induced an involuntary expulsion of urine for assessing or quantifying stress urinary incontinence in the patient.

2. The method according to claim 1, and further comprising assessing or quantifying stress urinary incontinence in the patient that arises from at least one of stroke, trauma, neurological diseases, neurological disorders, pre-operative recovery from anesthesia, and post-operative recovery from anesthesia.

* * * * *